(12) United States Patent
Watson et al.

(10) Patent No.: US 6,995,270 B2
(45) Date of Patent: Feb. 7, 2006

(54) HYDROGENATION PROCESS

(75) Inventors: Timothy James Norman Watson, Waterford, CT (US); Michael Girard Vetelino, North Stonington, CT (US)

(73) Assignee: Pfizer INC, New York, NY (US)

( * ) Notice: Subject to any disclaimer, the term of this patent is extended or adjusted under 35 U.S.C. 154(b) by 130 days.

(21) Appl. No.: 10/752,119

(22) Filed: Jan. 5, 2004

(65) Prior Publication Data

US 2004/0249160 A1 Dec. 9, 2004

Related U.S. Application Data

(60) Provisional application No. 60/455,604, filed on Mar. 17, 2003.

(51) Int. Cl.
*C07D 211/72* (2006.01)

(52) U.S. Cl. .................................................. 546/304
(58) Field of Classification Search ................ 546/304
See application file for complete search history.

(56) References Cited

U.S. PATENT DOCUMENTS 4,680,283 A 7/1987 Veber et al.

OTHER PUBLICATIONS

Hcaplus 52:21115.*

* cited by examiner

*Primary Examiner*—Cecilia J. Tsang
*Assistant Examiner*—Binta Robinson
(74) *Attorney, Agent, or Firm*—Steve T. Zelson; Jolene W. Appleman

(57) ABSTRACT

The invention is a process to hydrogenate an aryl-substituted pyridine, such as 2-phenyl-3-aminopyridine, without over-reducing the aryl ring using a specific Pt/C catalyst.

13 Claims, No Drawings

HYDROGENATION PROCESS

This application claims the benefit of Provisional Application No. 60/455,604, filed Mar. 17, 2003.

BACKGROUND OF THE INVENTION

1. Field of the Invention

The invention pertains to a hydrogenation process for preparing piperidine derivatives that minimizes undesirable by-products, increases yield, and simplifies manufacture in eliminating certain purifications otherwise required. In a preferred practice, a specific heterogeneous catalyst is used to hydrogenate an aryl-substituted pyridine, such as 2-phenyl-3-aminopyridine, whereby the pyridine is reduced to piperidine without over-reduction of the phenyl to cyclohexyl.

2. Description of the Prior Art

Piperidine derivatives are used in the synthesis of various compounds, including pharmaceuticals. For example, 2-phenyl-3-aminopyridine is employed as a reactant in the manufacture of antagonists having utility in treating diseases mediated by an excess of substance P. Substance P is a naturally occurring undecapeptide belonging to the tachykinin family of peptides, members of which exert prompt stimulatory action on smooth muscle tissue. It possesses a characteristic amino acid sequence as described in e.g. U.S. Pat. No. 4,680,283. The involvement of substance P and other tachykinins in the pathophysiology of numerous diseases is known in the art. E.g. substance P has been shown to be involved in the transition of migraine pain, as well as in: central nervous system (CNS) disorders including anxiety and schizophrenia; respiratory and inflammatory diseases such as asthma and rheumatoid arthritis; gastrointestinal disorders such as ulcerative colitis, irritable bowel syndrome and Crohn's disease. Substance P and other tachykinin antagonists have also been reported as useful in treating cardiovascular diseases, allergic conditions, immunoregulation, vascodilation, bronchospasm, reflex or neuronal control of the viscera, senile dementia of the Alzheimer's type, emesis, sunburn and *Helicobacter pylori* infection.

One particular aryl-substituted pyridine commonly employed in the manufacture of substance P antagonists is 2-phenyl-3-aminopyridine. Manufacture in this regard typically entails the hydrogenation of this compound to form 2-phenyl-3-aminopiperidine. Specifically, hydrogenation (or reduction) of the pyridine ring to piperidine is selectively desired over hydrogenation of the phenyl ring. Industrially, heterogeneous catalysts are preferred for this purpose, with platinum-on-carbon (Pt/C) catalysts being favored. While commercially viable, Pt/C catalysts used in this context heretofore nonetheless manifest certain shortcomings, including importantly the generation of unwanted by-products. For example, these prior catalysts can cause over-reduction of the 2-phenyl-3-aminopyridine starting material to unacceptable levels. Over-reduction in this use setting results in 2-cyclohexyl-3-aminopiperidine, which is caused by the hydrogenation of the phenyl to cyclohexyl. This by-product, when produced at levels known hitherto, in a large scale production facility, necessitates additional purification steps, such as recrystallization, in order that product specifications be met. For example, in a prior art practice approximately 12% to 15% of the 2-phenyl-3-aminopyridine starting material is over-reduced to 2-cyclohexyl-3-aminopiperdine.

The creation of such by-products causes inefficient use of starting material, lowered product yield, and complicates purification, necessitating additional steps to remove of these materials. Accordingly, there is a continuing need to develop a hydrogenation process that evinces less over-reduction, with amelioration of adverse consequences that otherwise attend.

SUMMARY OF THE INVENTION

The present invention addresses the foregoing need. In one practice, the invention is directed to a hydrogenation process which comprises contacting hydrogen with an aryl-substituted pyridine, such as 2-phenyl-3-aminopyridine, in the presence of a Pt/C type 18MA catalyst, preferably a 5% Pt/C type 18MA catalyst, under conditions effective to selectively hydrogenate the pyridine. In a preferred embodiment, no more than about 6% of starting material, e.g. 2-phenyl-3-aminopyridine, is over-reduced to unwanted by-products, e.g. 2-cyclohexyl-3-aminopiperdine.

DETAILED DESCRIPTION OF THE INVENTION

Aryl-substituted pyridine:

Aryl-substituted pyridines subject to the process of the present invention include those known in the art. Preferred pyridines include those useful in the preparation of pharmaceutical compounds such as substance P antagonists, including without limitation aryl-substituted aminopyridine, such as those having the formula:

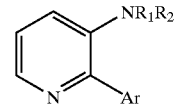

wherein $R_1$ and $R_2$ are each independently hydrogen or $C_{1-6}$ alkyl, each of which may independently be branched or normal; and Ar is a $C_{5-10}$ aryl such as phenyl, naphthyl, biphenyl, any of which may be optionally substituted with one or more $C_{1-4}$ alkyl groups.

Most preferably $R_1$ and $R_2$ are each hydrogen and Ar is phenyl, the pyridine being 2-phenyl-3-aminopyridine having the formula:

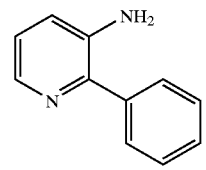

The Catalyst:

The catalyst employed in the inventive process is a Pt/C type 18MA catalyst commercially available from Johnson-Matthey plc, London, England. Preferably, the Pt loading on the carbon support is about 5%, such as the 5% Pt/C type 18MA obtainable from Johnson-Matthey as aforesaid. The catalyst may be employed in physical states known to the art, such as dry power or preferably paste, e.g. about 40% to about 50% water wet (w/w). Feed of the catalyst into the reactor may be by conventional means, such as by injection and metering devices known in the art.

Hydrogenation of the aryl-substituted pyridine substrate occurs by contacting same with hydrogen or other like reducing agent(s) suitable for the purpose in the presence of the type 18MA catalyst under conditions effective to selectively hydrogenate the pyridine ring. In addition to the inventive use of the Pt/C type 18MA catalyst in the process, conditions effective in this regard are further understood by the artisan to include those process parameters which favor the reduction of the pyridine ring as opposed to the reduction of its aryl substituent. As also appreciated by the artisan, the term connotes an end point for the selective hydrogenation reaction, i.e. once a desired or final amount of 2-phenyl-3-aminopyridine has been selectively obtained, the reaction must be seasonably terminated lest further reduction, now of the phenyl ring, occur whereby the unwanted 2-phenyl-3-aminopiperidine by-product is produced. Conditions of time, temperature, pressure, reactant, reactant vessel and catalytic amounts as well as other process parameters whereby hydrogenation including selective hydrogenation known heretofore manifests may be in accord with conventional practices.

By way of example only, such parameters typically include: a reactor system, e.g. a continuous reactor(s) or preferably a batch reactor(s) such as stirred autoclave reactor of suitable materials of construction e.g. Hastelloy and the like; reducing atmospheres (e.g. $H_2$) of up to 100 psig, preferably about 40 to about 100 psig, about 50 to about 90 psig more preferred; temperatures of about 10° C. to about 25° C., preferably about 18° C. to about 25° C.; reaction times can vary as appreciated by the artisan and delineated herein; for batch reactions times of about 0.5 to about 2 hrs are typical in a most preferred embodiment, a batch mode is used under conditions of a relatively low temperature (e.g. about 18° C. to about 22° C.) and relatively high pressure (e.g. about 80 to 90 psig). In a preferred practice of the invention, no more than about 6% of the aryl-substituted pyridine starting material, e.g., 2-phenyl-3-aminopyrrdine is converted to the over-reduced 2-cyclohexyl-3-aminopiperidine; more preferably no more than about 5% e.g. about 3% to about 5% of said conversion occurs.

The process preferably occurs in the presence of one or more solvents, including those known in the art for hydrogenation generally. Preferably, the solvent is polar, more preferably having one or more hydroxyl groups, e.g. water and alcohols such as methanol, ethanol, isopropanol (IPA) and the like. It is further preferred if the solvent is or is rendered acidic. Examples of serviceable solvents include aqueous acidic solvents such as 10% HCl/water (water+10% v/v concentrated HCl) which is most preferred, and 10% HCl/IPA.

For purposes of convenience, the invention will now be described in the context of selectively hydrogenating 2-phenyl-3-aminopyridine to form 2-phenyl-3-aminopiperidine. Adaptation of the succeeding description to other aryl-substituted pyridines as contemplated within the scope of the invention is within the ready ken of the artisan.

The following examples are illustrative of the present process; they are not to be construed as limiting the scope or practice of the invention.

EXAMPLE 1

Demonstrates, in a pilot plant, an embodiment of the invention wherein 2-phenyl-3-aminopyridine was hydrogenated by contact with hydrogen in the presence of a 5% Pt/C type 18MA catalyst. In a series of runs, approximately 8 kg of a 50% water wet catalyst paste formed of 5% Pt/C type 18MA catalyst was fed into a stirred autoclave reactor (Hastelloy C). The paste was formed by admixing approximately 4 kg of the dry catalyst with an amount of water commensurate yield to 50% water wet paste. Thereafter approximately 9 kg of 2-phenyl-3-aminopyridine in a solution of 10% HCl/water was fed into the reactor, charged with $H_2$ at a pressure of about 80 to about 90 psig. Reaction temperature was approximately 180 to about 22°. The reaction proceeded for about 0.5 to about 7.0 hr, after which effluent from the reactor was sampled and analyzed in a HP-5 gas chromatograph (GC). An area percent report indicative of product amounts was generated. As appreciated by the artisan, a GC area percent correlates directly to amount of underlying product.

In a first run, the area % for the desired product 2-phenyl-3-aminopiperidine was about 87.9% whereas that for the unwanted by-product of over-reduction, 2-cyclohexyl-3-aminopiperidine, was about 3.5%.

In a second run, the area % for the desired product 2-phenyl-3-aminopiperidine was about 89.2% whereas that for the unwanted by-product of over-reduction, 2-cyclohexyl-3-aminopiperidine, was about 5.1%.

COMPARATIVE EXAMPLE 1

Demonstrates the prior art. The same conditions as in Example 1 were employed but for the use of Catalyst A, a 5% Pt/C catalyst (not type 18MA) previously used in the art to hydrogenate 2-phenyl-3-aminopyridine to form 2-phenyl-3-aminopiperidine. GC values and area percent were assessed as in Example 1.

In a first comparative run, the area % for the desired product 2-phenyl-3-aminopiperidine was about 83.2% whereas that for the unwanted by-product of over-reduction, 2-cyclohexyl-3-aminopiperidine, was about 10.2%.

In a second comparative run, the area % for the desired product 2-phenyl-3-aminopiperidine was about 84.5% whereas that for the unwanted by-product of over-reduction, 2-cyclohexyl-3-aminopiperidine, was about 9.1%.

The above results show a dramatic decrease in unwanted by-product via the inventive process as well as a concurrent increase in product yield. That is, in the inventive embodiment exemplified, the undesired production of 2-cyclohexyl-3-aminopiperidine impurity was reduced by over 50% on average whereas at the same time the sought-after product, 2-phenyl-3-aminopiperidine, showed an increase in overall yield.

What is claimed:

1. A hydrogenation process comprising contacting hydrogen with an aryl-substituted pyridine in the presence of a Pt/C type 18MA catalyst under conditions effective to selectively hydrogenate the pyridine.

2. The process of claim 1 wherein said catalyst has a Pt loading of about 5%.

3. The process of claim 1 wherein the aryl-substituted pyridine is an aryl-substituted aminopyridine.

4. The process of claim 3 wherein said aryl-substituted aminopyridine has the formula:

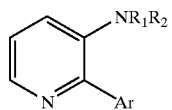

wherein $R_1$ and $R_2$ are each independently hydrogen or $C_{1-6}$-alkyl; and Ar is a $C_{5-10}$ aryl which may be optionally substituted with one or more $C_{1-4}$ alkyl groups.

5. The process of claim 4 wherein said aryl-substituted aminopyridine is as 2-phenyl-3-aminopyridine.

6. The process of claim 1 wherein said contact occurs in the presence of a solvent.

7. The process of claim 6 wherein said solvent is an aqueous acidic solvent or an alcoholic acidic solvent.

8. The process of claim 7 wherein said solvent is aqueous HCl.

9. A hydrogenation process comprising contacting hydrogen with 2-phenyl-3-aminopyridine in the presence of a 5% Pt/C type 18MA catalyst and a 10% HCl/water solvent under conditions effective to selectively hydrogenate the pyridine to produce 2-phenyl-3-aminopiperidine.

10. The process of claim 9 wherein 2-cyclohexyl-3-aminopiperidine produced as a by-product of over-reduction is present at the end of said hydrogenation at an amount of no more than about 6% of the amount of 2-phenyl-3-aminopyridine employed at the start of said hydrogenation.

11. The process of claim 10 wherein hydrogenation occurs at a temperature of about 15° C. to about 25° C.

12. The process of claim 11 wherein hydrogenation occurs at a pressure of about 40 to about 100 psig.

13. A process for minimizing the over-hydrogenation of an aryl-substituted pyridine which comprises contacting hydrogen and an aryl-substituted pyridine with a Pt/C type 18MA catalyst under conditions effective to selectively hydrogenate the pyridine ring.

* * * * *